United States Patent [19]

Roman

[11] 4,219,565

[45] Aug. 26, 1980

[54] OXYIMINO-SUBSTITUTED CYCLOPROPANECARBOXYLATE PESTICIDES

[75] Inventor: Steven A. Roman, Oakdale, Calif.

[73] Assignee: Shell Oil Company, Houston, Tex.

[21] Appl. No.: 52,157

[22] Filed: Jun. 26, 1979

[51] Int. Cl.$^2$ .................. C07C 13/02; A01N 9/20
[52] U.S. Cl. .................. 424/305; 560/35; 560/118; 560/124; 562/440; 562/500; 562/506
[58] Field of Search ............ 560/118, 124, 35; 424/306, 305

[56] References Cited

U.S. PATENT DOCUMENTS

| | | | |
|---|---|---|---|
| 3,567,740 | 3/1971 | Matsui | 260/347.4 |
| 3,683,005 | 8/1972 | Sota | 560/124 |
| 3,792,079 | 2/1974 | Orazio | 560/124 |
| 3,922,269 | 11/1975 | Elliot | 260/347.4 |

Primary Examiner—Robert Gerstl

[57] ABSTRACT

A cyclopropane compound having the formula

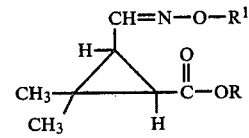

wherein
R is a residue of certain alcohols; and
R$^1$ is hydrogen, or certain optionally halogenated hydrocarbyl groups, are highly active pesticides.

9 Claims, No Drawings

OXYIMINO-SUBSTITUTED CYCLOPROPANECARBOXYLATE PESTICIDES

BACKGROUND OF THE INVENTION

1. Field of the Invention

This invention is directed to new oxyimino-substituted compounds, their use as pesticides, to pesticidal formulations containing these new compounds and to certain novel intermediates.

2. Description of the Prior Art

U.S. Pat. No. 3,922,269 describes a class of 2,2-dimethyl-3-(oxyiminomethyl)cyclopropanecarboxylic acid esters with certain alcohols which are useful as insecticides. U.S. Pat. Nos. 3,567,740 and 3,683,005 describe esters of certain other cyclopropanecarboxylic acids with substituted benzyl or 4-phenylbutenyl alcohols.

SUMMARY OF THE INVENTION

It has now been found that certain oxyimino-substituted cyclopropanecarboxylates derived from 2,2-dimethyl-3-formyl-cyclopropanecarboxylic acid and ring-substituted benzyl alcohols or substituted alkenols are useful pesticides (insecticides and acaricides) and exhibit high knockdown characteristics.

Therefore, this invention is directed to new cyclopropane compounds having the formula

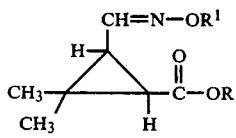

wherein $R^1$ represents a hydrogen atom, an alkyl group, straight chain or branched, containing from 1 to 10 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or alkynyl group containing from 3 to 4 carbon atoms or an aryl group containing from 6 to 12 carbon atoms or an aralkyl group containing from 7 to 10 carbon atoms, each optionally ring-substituted by one or more halogen atoms; and R is a group of the formula I-III

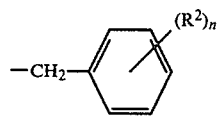

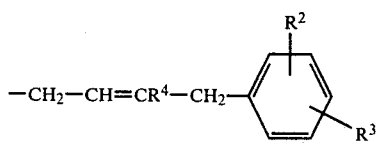

or

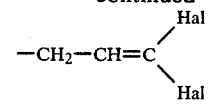

wherein $R^2$ and $R^3$ each independently is a hydrogen atom, a halogen atom having an atomic number of from 9 to 35, inclusive, an alkyl group containing from 1 to 4 carbon atoms or a nitro group, each Hal is independently a halogen atom, $R^4$ is a hydrogen atom or a halogen atom and n is an integer of from 1 to 5.

In the above formulas, suitable halogen atom substitutents are chlorine, fluorine or bromine.

Since the biological activity of various optical or geometric isomers and diastereoisomer pairs within the esters of the invention may differ somewhat, it may be desirable to use a more active optical and/or geometric isomer or diastereoisomer pair of the invention substantially free of the other isomers or pair. Generally speaking, because of their level of pesticidal activity, the (1R, cis) esters are preferred, although the (1R,trans) are also very active.

The oxime substituent group of the compounds of the invention gives rise to geometric isomerism by virtue of the presence of an asymmetrically substituted double bond. These isomers are usually described as follows:

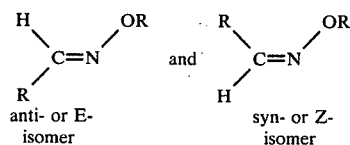

anti- or E-isomer    syn- or Z-isomer

A useful subclass of the invention comprises esters in which the oxime substituent is in the Z-isomer form as such isomers can be several times more pesticidally active than when the oxime substituent is in the E-isomer form or is a mixture of the E- and Z-isomer forms.

Typical examples of species within the scope of the invention are:

3-chloro-3-fluoropropen-2-yl (1R,trans)-2,2-dimethyl-3-((sec-butoxyimino)methyl)-cyclopropanecarboxylate, 3-chloro-4-phenyl-2-buten-1-yl 2,2-dimethyl-3-((proparagyloxyimino)methyl)-cyclopropanecarboxylate, 2,6-dibromobenzyl (1R,cis)-2,2-dimethyl-3-((isobutoxyimino)-methyl)-cyclopropanecarboxylate, 2,4,6-trimethylbenzyl (1R,trans)-2,2-dimethyl-3-(trifluoromethoxyimino)methyl)-cyclopropanecarboxylate and 4-Nitrobenzyl (1R,cis)-2,2-dimethyl-3-((p-chlorophenoxyimino)-methyl)cyclopropanecarboxylate.

Because of their pesticidal utility in agricultural and domestic situations, preferred compounds of the invention are those wherein R is pentachlorobenzyl, 3-nitrobenzyl, 2,6-dichlorobenzyl, 2,6-difluorobenzyl, 2-chloro-6-fluorobenzyl or 3,3-dichloropropen-2-yl and $R^1$ is an alkyl group containing from 1 to 6 carbon atoms, a (cycloalkyl)alkyl group containing from 3 to 6 ring carbon atoms, a total of from 4 to 8 carbon atoms and optionally ring-substituted by from 1 to 4 chlorine, fluorine and/or bromine atoms, a cycloalkyl group containing from 3 to 6 ring carbon atoms, an alkenyl group containing from 3 to 4 ring carbon atoms optionally substituted by one or two chlorine, fluorine and/or bromine atoms or an alkynyl group containing from 3 to 4 carbon atoms, an aryl group containing from 6 to 12 carbon atoms or an aralkyl group containing from 7 to 10 carbon atoms.

In the pesticidal esters of the invention, R preferably represents pentachlorobenzyl or 2,6-dichlorobenzyl, $R^1$ preferably represents an alkyl group containing 2 to 6 carbon atoms, such as ethyl, n-propyl, isopropyl, n-butyl, sec-butyl, isobutyl, tert-butyl, amyl, isoamyl, tert-amyl, n-hexyl and the like, a (cycloalkyl)alkyl group containing from 3 to 6 ring carbon atoms and a total of from 4 to 8 carbon atoms, such as cyclopropylmethyl, 1-(cyclopropyl)ethyl, cyclohexylmethyl and the like, a cycloalkyl group containing 3 to 6 ring carbon atoms, such as cyclopropyl, cyclobutyl, cyclopentyl or cyclohexyl and the like, an alkenyl or alkynyl group containing 3 to 4 carbon atoms such as allyl or propargyl and the like, an aryl group containing from 6 to 10 carbon atoms such as phenyl or an aralkyl group containing from 7 to 10 carbon atoms, such as benzyl, phenethyl or the like.

Preferred because of their pesticidal properties are those esters wherein $R^1$ is an alkyl group containing from 2 to 6 carbon atoms, a (cycloalkyl)alkyl or cycloalkyl group containing 4 to 5 carbon atoms, allyl, phenyl or benzyl. Particularly suitable are those compounds where $R^1$ is an alkyl, (cyclopropyl)alkyl or cycloalkyl group containing 4 to 5 carbon atoms, particularly n-butyl, isobutyl, tert-butyl, n-pentyl, cyclopentyl, (cyclopropyl)methyl or (cyclobutyl)methyl.

Because of their pesticidal activity and ease of preparation, one preferred subclass of the invention are those esters wherein R is derived from 2,6-dichlorobenzyl alcohol. Examples of some highly active compounds of this subclass of the invention are:
2,6-dichlorobenzyl (1R,cis)-2,2-dimethyl-3-((cyclopropylmethoxyimino)methyl)cyclopropanecarboxylate and
2,6-dichlorobenzyl (1R,cis)-2,2-dimethyl-3-(isobutoxyimino)-methyl)cyclopropanecarboxylate.

Because of their pesticidal activity, another preferred subclass of the invention are those esters derived from pentachlorobenzyl alcohol. Examples of some highly active compounds of this subclass of the invention are the following compounds wherein $R^1$ is an alkyl, (cycloalkyl)alkyl or cycloalkyl group containing 4 to 5 carbon atoms:
pentachlorobenzyl (1R,cis)-2,2-dimethyl-3-((cyclopropylmethoxyimino)methyl)cyclopropanecarboxylate,
pentachlorobenzyl (1R,cis)-2,2-dimethyl-3-((n-butoxyimino)-methyl)cyclopropanecarboxylate,
pentachlorobenzyl (1R,cis)-2,2-dimethyl-3-((isobutoxyimino)-methyl)cyclopropanecarboxylate,
pentachlorobenzyl (1R,cis)-2,2-dimethyl-3-((tert-butoxyimino)methyl)cyclopropanecarboxylate, and
pentachlorobenzyl (1R,cis)-2,2-dimethyl-3-((n-pentoxyimino)-methyl)cyclopropanecarboxylate, and
pentachlorobenzyl (1R,cis)-2,2-dimethyl-3-((cyclopentoxyimino)methyl)cyclopropanecarboxylate.

It has been generally observed that esters, wherein the oxime substituent is in the Z-iosmer form, are the most pesticidally active. Therefore, the Z-isomers (or mixtures of isomers in which the Z-isomer predominates) form another preferred subclass of the esters of the invention. That the Z-isomer form is more pesticidally active contrasts with another class of oxime pesticides disclosed in U.S. Pat. 4,079,149, in which the E-isomer form is said to be the more pesticidally active of the oxime geometric isomer forms.

Because of their useful pesticidal properties, one preferred class of esters of the invention comprises those compounds wherein $R^1$ is (cycloalkyl)alkyl and R is one of the groups of formulas I–III. Particularly preferred are esters wherein $R^1$ is cyclopropylmethyl, and R is 2,6-dichlorobenzyl or pentachlorobenzyl or individual diastereoisomers of such esters.

The pesticidal esters of the present invention may be prepared by esterification involving the reaction of an alcohol or derivative thereof of formula RQ e.g., of formula IV–VI, and a cyclopropane carboxylic acid or derivative thereof of formula VII

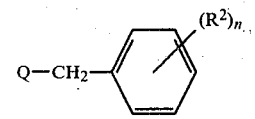   IV

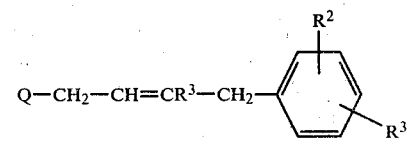   V

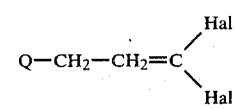   VI

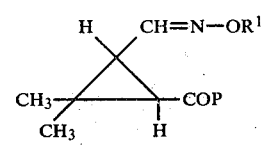   VII where Q and COP are functional groups or atoms which will react to form an ester linkage and $R^2$, $R^3$, $R^4$ and Hal are as defined above.

It is usually convenient in practice either to treat the acid or acid halide with the alcohol (COP=COOH or CO-halide and Q=OH) or to treat a halogeno compound (Q=halogen) with a salt of the carboxylic acid (COP=COO—M where M is, for example, a silver or triethylammonium cation).

Transesterification is not always practical and, it is useful to prepare the intermediate alkyl ester as a tert-butyl ester (R=tert-butyl) which can be selectively converted (under acid conditions) to give the free acid, which can, after conversion to the acid halide by methods known in the art, be esterified to a pesticidal ester.

The alkyl esters of the present invention can also be prepared by treating an ester of caronaldehyde of formula XI

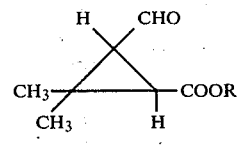   XI where R is an alkyl group, with hydroxylamine or an O-substituted hydroxylamine of formula $R^1ONH_2$ where $R^1$ is as defined above, and in the case where $R^1$ represents hydrogen, subsequently hydrocarbylating the resulting oxime, if desired, with an alkyl (or alkenyl)

halide or the like, to give an alkoxime (or alkenyloxime), etc. Oxime formation can take place by treating substantially equimolar amounts of aldehyde and hydroxylamine or hydrocarbyloxyamine in a polar solvent such as an alkanol, e.g., ethanol or dioxane. When the aldehyde is converted into the oxime by reaction with hydroxylamine and it is desired to convert the resulting oxime into an alkylated or alkenylated derivative or the like, this reaction may be carried out by procedures customarily used for the alkylation of phenols. Thus, the oxime may be treated in a polar solvent, such as ethanol, with an alkyl halide, typically the bromide, in the presence of a hydrogen halide acceptor and the mixture heated until reaction is complete.

Oxime formation is normally carried out using an acid addition salt of hydroxylamine or the hydrocarbyloxyamine, e.g., the hydrochloride. In the cases where it is desired to prepare a compound where $R^1$ represents methyl, the availability of methoxylamine hydrochloride makes it generally more convenient to carry out the reaction in one step using methoxylamine hydrochloride, but when compounds are required where $R^1$ represents a larger group, it is usually more convenient to form the oxime first and subsequently to hydrocarbylate the oxime.

Alternatively, in another modification, the compounds of the invention are prepared by treating (1R,cis)-caronaldehydic acid previously described in U.S. Pat. No. 3,723,469 with an O-substituted hydroxylamine salt of the formula $R^1ONH_3$—W wherein $R^1$ is as defined above and W is the anion of salt-forming inorganic or organic acid. Suitable inorganic acids include hydrohalogenic acids such as hydrochloric and hydrobromic, sulfur acids such as sulfuric, fluorosulfonic, phosphorus acids such as phosphoric, and nitrogen acids such as nitric acid, or boron acids such as boric or fluoboric acid. Organic acids, such as oxalic, malonic and succinic acids, are also suitable.

The reaction is preferably conducted in an aqueous medium in the presence of a buffer, such as an alkali metal salt of a polybasic acid, including sodium hydrogen carbonate, potassium hydrogen tartrate, disodium hydrogen phosphate and the like. Generally, at least one mole of buffer is used for each mole of (1R,cis)-caronaldehydic acid.

The molar ratio of reactants is not critical and can be widely varied, generally a molar ratio of the O-substituted hydroxylamine salt to (1R,cis)-caronaldehydic acid is suitably from about 1.0 to about 1.5 and preferably from about 1.02 to about 1.3.

The reaction is generally conducted in the liquid phase by agitating, e.g., stirring, a mixture of the reactants. The resulting product is recovered by conventional techniques such as filtering, extracting or the like.

The reaction temperature is not critical and can easily range from ambient to the reflux temperature of any solvent employed at normal pressure. Generally, the temperature is between about 0° C. to about 50° C.

A minor amount of co-solvent can be used in the reaction medium. Suitable co-solvents are lower alcohols containing from 1 to 6 carbon atoms, such as methanol, ethanol and the like.

The resulting (1R,cis)-acids are converted to the ester compounds of the invention, for example, by reaction with the arylmethyl halide, in the presence of triethylamine, in a solvent, such as refluxing ethyl acetate. However, two-phase-transfer systems are preferred for esterification, particularly using onium catalysts, such as those disclose in U.S. Pat. No. 4,110,360. Toluene is the preferred solvent for the organic phase with tetrabutylammonium sulfate and benzyltriethylammonium chloride the preferred catalyst.

The alcohols from which the substituent R is derived are known in the art as, for example, in U.S. Pat. Nos. 3,567,740 and 3,683,005 and Hatch et al, *J. Amer. Chem. Soc.*, 79, pages 3091–3 (1957).

An isomer mixture of the esters of the invention are readily separated into the individual diastereoisomers using known procedures, as for example, by preparative scale liquid chromatography. One such chromatographic system which can be employed has the following characteristics:

Column—porisil polar bonded phase, 9.2×250 mm;
  Mobile Phase—8% v/v diethyl ether in n-hexane;
  Flow Rate—2.5 ml/min;
  Detection—$UV_{254}$ at 2.0 AUFS;
  Injection—typically 500 ml of a 20 mg/ml solution in the mobile phase.

Such a procedure readily yields the single diastereoisomers in greater than 90% purity (as determined by NMR analysis), e.g. from the (1R,cis)-isomer mixture.

Since it has been discovered that the esters of the invention in which the oxime substituent is in the Z-isomer form are pesticidally more active than when the oxime substituent is in either the E-isomer form or is a mixture of E- and Z-isomer forms, it can be desirable to convert the esters in E-isomer form into a mixture of esters in both the E- and Z-isomer forms. Such conversion is accomplished by the addition of a minor amount of an organic or inorganic acidic material. Any inorganic or organic acid or acidic acting material can be used, including acidic clays such as acidic silicates and aluminates or synthetic acidified clays, mineral acids such as hydrochloric or sulfuric acid, sulfonic acids such as toluenesulfonic acid, or organic acids, including lower alkanoic acids such as acetic, propionic or butyric acids. The acid can be used in a solid or liquid form. While the precise amount of acid used to convert the E-isomer or Z-isomer into the E- and Z-isomer mixture can vary depending on the particular oxyimino-substituted ester, form 0.001 to 5% by weight of acid based on the E-isomer or Z-isomer is generally sufficient. Preferably, from 0.01 to 5% by weight of acid is used.

The invention includes, within its scope, pesticidal compositions comprising a pesticidally acceptable adjuvant—that is, at least one carrier or a surface-active agent—and, as active ingredient, at least one pesticidally active ester of this invention. Likewise, the invention includes also a method of combatting insect, acarine or other arthropod pests at a locus which comprises applying to the pests or to the locus a pesticidally effective amount of at least one compound of the invention.

With respect to the spectrum of pesticidal activity, the compounds of this invention exhibit a selective or non-selective activity on such orders as Coleoptera, Lepidoptera (especially larvae), Diptera, Orthoptera, Hemiptera, Homoptera and Acarina depending upon a specific combination of acid and an alcohol according to the present invention. The compositions according to the present invention are very useful for controlling disease carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamondback moths (*Plutella maculipennis* Curtis), imported cabbage worm (*Pieris rapae* Linne), rice stem borers (*Chilo suppressalis* Walker), corn earworm larvae (*Heliothis zea* Boddie), aphids, tortrixes, leaf-miners and the like.

The esters are used for harvested crops, horticultural application, forests, cultures in green house, packaging materials for foodstuffs, in household applications and as ectoparasiticides.

The term "carrier" as used herein means a material, that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mono-, di- and trialkyl-amines; condensates of these with ethylene oxide and/or proplyene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by extrusion of plastics, agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, nonsedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethylhexyl)bicyclo-[2,2,1]hept-5-ene-2,3-dicarboximide, octachlorodipropyl ether, isobornyl thiocyanoacetate, and other synergists used for allethrin and pyrethrin. Useful compositions can be prepared with other biological chemicals including other cyclopropanecarboxylates, organic phosphate type insecticides and carbamate type insecticides.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order or 0.01% to 0.5% based on the total weight of the formulation, though under some circumstances the effective concentration will be as little as 0.001% or as much as 2%, on the same basis.

The superior activity of the (1R,cis) esters of the invention is usefully employed when such an ester is present in an amount substantially greater than that usually present in the racemate of an oxyimino substituted ester. Therefore, use of the (1R,cis) esters of the invention in a form substantially free of other stereoisomers is preferred, for example in a (1R,cis) isomer purity of greater than about 85%, preferably in a (1R,cis) isomer purity greater than about 90% or even greater than 95%.

ILLUSTRATIVE EMBODIMENTS

The invention is illustrated by the following embodiments which describe the preparation and biological testing of typical species of the invention with respect to representative insects and acarines. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT 1

(1R,cis(-2,2-dimethyl-3-((isobutoxyimino)methyl)cyclopropanecarboxylic acid

A solution of 1.7 g of (1R,cis)-caronaldehydic acid and 1.6 g of isobutoxyamine hydrochloride in 50 ml of water was stirred at room temperature for 5 hours in the presence of 2.2 g of sodium bicarbonate. The resulting mixture was filtered through celite, the filtrate was acidified with concentrated hydrochloric acid, the resulting solution was extracted with methylene chloride, and the combined extracts were dried over magnesium sulfate and stripped to give 2.4 g of desired product as an oil; $[\alpha]_D^{25}+33.2°$ (CHCl$_3$; c=0.02 g/cc).

EMBODIMENT 2

(1R,cis)-2,2-dimethyl-3-((cyclopropylmethoxyimino)-methyl)-cyclopropanecarboxylic acid A solution of 1.7 g of (1R,cis)-caronaldehydic acid and 1.6 g of cyclopropylmethoxyamine hydrochloride in 50 ml of water was stirred at room temperature for about 4 hours in the presence of 2.2 g of sodium bicarbonate. The resulting mixture was filtered through celite and the filtrate was acidified to pH 4 with concentrated hydrochloric acid. The resulting solution was extracted with methylene chloride and the combined extracts were dried over magnesium sulfate and stripped to give 2.0 g of the desired product as an oil; $[\alpha]_D^{25}+30.0°$ (CHCl$_3$; c=0.02 g/cc).

Following procedures similar to Embodiments 1 and 2 above: (1R,cis)-2,2-dimethyl-3-((cyclobutoxyimino)-methyl)cyclopropanecarboxylic acid was prepared.

EMBODIMENT 3

Pentachlorobenzyl (1R,cis)-2,2-dimethyl-3-((cyclobutoxyimino)methyl)cyclopropanecarboxylate To a solution of 0.4 g potassium carbonate, 0.05 g tetrabutylammonium sulfate and 0.05 g benzyltriethylammonium chloride in 6 ml of water was added 1.30 g of (1R,cis)-2,2-dimethyl-3-((cyclobutoxyimino)methyl)cyclopropanecarboxylic acid in 10 ml toluene and then 1.64 g of pentachlorobenzyl chloride. The resulting mixture was heated at 60°–80° with vigorous stirring for several days.

The toluene phase was separated, washed successively with water, sodium bicarbonate solution and saturated sodium chloride solution, dried over magnesium sulfate and stipped to yield an oil. The product was chromatographed using pentane:ether (4:1) as the eluent to give an amber oil which crystallized on standing. This product was recrystallized from pentane to yield 1.4 g of solid; m.p. 78°–86° C.; $[\alpha]_D^{25}=-22.5$ (CHCl$_3$) 0.02 g/cc.

EMBODIMENTS 4–8

Following procedures similar to Embodiment 3 above, the additional (1R,cis)-2,2-dimethyl-3-oxyimino)methyl)-cyclopropanecarboxylates were prepared as set forth in Table 1.

Table 1

OXYIMINO-SUBSTITUTED CYCLOPROPANECARBOXYLATES

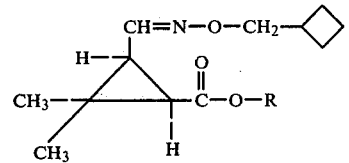

| Embodiment | R | $[\alpha]_D^{25}$ (CHCl$_3$) | % Yield |
|---|---|---|---|
| 4 | 3-nitrobenzyl | +50.0 | 65 |
| 5 | 2,6-dichlorobenzyl | −18.8 | 90 |
| 6 | 2,6-difluorobenzyl | −7.5 | 95 |
| 7 | 2-chloro-6-fluorobenzyl | −12.5 | 80 |
| 8 | 3,3-dichloro-propen-2-yl | +22.5 | 67 |

Following procedures similar to Embodiments 1–8 above the corresponding racemic and (1R,trans) compound are prepared, as well as carboxylate, 2,6-dibromobenzyl 2,2-dimethyl-3-((n-pentoxyimino)methyl)-cyclopropanecarboxylate, pentafluorobenzyl-2,2-dimethyl-3-((cyclopentoxyimino)methyl)cyclopropanecarboxylate, 2,4,6-tribromobenzyl 2,2-dimethyl-3-((n-propoxyimino)methyl)cyclopropanecarboxylate, and 3,3-dibromopropen-2-yl 2,2-dimethyl-3-((isopropoxyimino)methyl)cyclopropanecarboxylate in the racemic, (1R,cis) and (1R,trans) forms.

EMBODIMENT 9

Pesticidal Activity

As an example, the activity of the compounds of this invention with respect to pests was determined by using standardized test methods to test the toxicity of the compounds as follows:

Corn earworm larvae (*Heliothis zea* Boddie) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the mortality in the test insects or acarine. Assigning the standard pesticide an arbitrary rating of 100, the toxicities of the compounds of the invention were expressed in terms of the toxicity indexes, which compares the toxicity of the compounds of the invention with that of the standard pesticide. That is to say, a test compound having a Toxicity Index of 200 would be twice as active as the standard pesticide.

Results of the above tests are shown in Table 2.

Table 2

PESTICIDAL ACTIVITY OF 3-((OXYIMINO)METHYL)-
CYCLOPROPANECARBOXYLATE EXPRESSED
AS TOXICITY INDEX
RELATIVE TO THAT OF PARATHION AS A
STANDARD EQUAL TO 100

| Embodiment | Corn Earworm |
|---|---|
| 3 | 150 |
| 4 | 13 |
| 5 | 88 |
| 6 | 35 |
| 7 | 37 |
| 8 | 17 |

I claim:

1. A compound of the formula

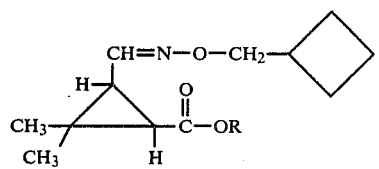

wherein R is pentachlorobenzyl or 2,6-dichlorobenzyl.

2. A compound according to claim 1 wherein R is pentachlorobenzyl.

3. A compound according to claim 1 wherein R is 2,6-dichlorobenzyl.

4. A compound according to claims 1, 2 or 3 in the (1R,cis) form.

5. A pesticidal composition comprising a pesticidally effective amount of an oxyimino-substituted cyclopropane compound according to claim 1 and at least one agriculturally acceptable surface-active agent or carrier therefore.

6. A method of controlling pests at a locus which comprises applying to the pests or to the locus a pesticidally effective amount of an oxyimino-substituted cyclopropane carboxylate according to claim 1.

7. A method according to claim 6 wherein the pests are selected from the order of Coleoptera, Lepidoptera, Diptera, Orthoptera, Hemiptera, Homoptera, or Acarina.

8. A method according to claim 6 wherein in the pests are larvae of the order Lepidoptera.

9. A method according to claim 6 wherein the pests are of the order Acarina.

* * * * *